United States Patent [19]
Glenn et al.

[11] Patent Number: 6,110,867
[45] Date of Patent: Aug. 29, 2000

[54] METHOD FOR PROVIDING ENHANCED PHOTOSYNTHESIS

[75] Inventors: David Michael Glenn, Shepherdstown, W. Va.; Dennis G. Sekutowski, Stockton, N.J.; Gary J. Puterka, Shepherdstown, W. Va.

[73] Assignee: Engelhard Corporation, Iselin, N.J.

[21] Appl. No.: 08/972,659

[22] Filed: Nov. 18, 1997

Related U.S. Application Data

[63] Continuation-in-part of application No. 08/812,301, Mar. 5, 1997, Pat. No. 5,908,708.

[51] Int. Cl.$^7$ .......................... A01N 59/00; A01N 59/06; A01N 55/02; A01N 57/00
[52] U.S. Cl. .......................... 504/119; 504/120; 504/126; 504/127; 504/187; 504/188; 71/DIG. 1
[58] Field of Search .................................... 504/119, 120, 504/126, 127, 188, 187; 71/DIG. 1

[56] References Cited

U.S. PATENT DOCUMENTS

| | | | |
|---|---|---|---|
| 2,441,423 | 5/1948 | Elliott et al. | 252/75 |
| 2,818,340 | 12/1957 | Goddin et al. | 99/2 |
| 2,948,632 | 8/1960 | Albert et al. | 514/465 |
| 3,120,445 | 2/1964 | Aluisi et al. | 106/286 |
| 3,124,505 | 3/1964 | Doyle et al. | 514/217 |
| 3,159,536 | 12/1964 | Marotta | 167/12 |
| 3,227,657 | 1/1966 | Haden, Jr. et al. | 252/75 |
| 3,235,451 | 2/1965 | Odeneal | 167/42 |
| 3,346,507 | 10/1967 | Taulli | 252/430 |
| 3,964,649 | 6/1976 | Alexander | 222/399 |
| 4,071,374 | 1/1978 | Minton | 252/75 |
| 4,203,864 | 5/1980 | Sawyer, Jr. | 252/431 |
| 4,274,883 | 6/1981 | Lumbeck et al. | 106/308 |
| 4,279,895 | 7/1981 | Carle | 424/127 |
| 4,382,868 | 5/1983 | House | 252/491 |
| 4,632,936 | 12/1986 | Boase et al. | 514/465 |
| 4,634,463 | 1/1987 | Ohsuga | 71/64 |
| 4,705,816 | 11/1987 | Pole | 523/524 |
| 5,122,518 | 6/1992 | Vrba | 514/63 |
| 5,186,935 | 2/1993 | Tucker | 424/410 |
| 5,392,559 | 2/1995 | Long | 43/52 |
| 5,393,461 | 2/1995 | Fillipova | 252/22 |
| 5,414,954 | 5/1995 | Long | 43/121 |
| 5,455,220 | 10/1995 | Dedolph | 71/64 |
| 5,480,638 | 1/1996 | Erwin | 424/614 |
| 5,597,400 | 1/1997 | Nonomura et al. | 71/28 |
| 5,628,144 | 5/1997 | Eastin | 47/58 |

FOREIGN PATENT DOCUMENTS

| | | |
|---|---|---|
| 002067948 | 8/1974 | Germany . |
| 53-127134 | 11/1978 | Japan ............. A01G 13/02 |
| 58-065201 | 4/1983 | Japan . |
| 1792257 A3 | 6/1990 | U.S.S.R. . |

OTHER PUBLICATIONS

Driggers, B. F. "Experiments with Talc and Other Dusts Used Against Recently Hatched Larvae of the Oriental and Codling Moths," J. Econ. Ent., 22 327–334 (1929).

Hunt, C.R., "Toxicity of Insecticide Dust Diluents and Carriers to Larvae of the Mexican Bean Beetle," J. Econ. Ent., 40 215–219 (1947).
P. Alexander, J.A. Kitchener and H.V. A. Briscoe, "Inert Dust Insecticides," Parts I, II, and III, Ann. Appl. Biol., 31 143–159 (1944).
W. Ebeling, R. F. Wagner "Rapid Desiccation of Drywood Termites with Inert Sorptive Dusts and Other Substances," J Econ. Ent., 52 190–207 (1959).
J.S. Dhaliwal, "Effect of Rainfall and Kaolinite Spray on the Corn Aphid, *Rhopalosiphum Maidis* (Fitch) Infesting Barley (*Hordeum Vulgare* Linn)," Forage Res. 5:155–157 (1979).
A. Boyce, "Mortality of Rhagoletis Completa Cress. (Diptera:Trypetidae) Through Ingestion of Certain Solid Materials," J. Econ Ent 25 1053–1059 (1932).
C. Richardson L. Glover, "Some Effects of Certain 'Inert' and Toxic Substances Upon the Twelve–Spotted Cucumber Beetle, *Diabrotica Duodecimpunctata,*" J Econ Ent 25 1176–1181 (1932).
A. Farmer, "The Effects of Dust on Vegetation: A Review," Envir Pol 79 (1193) 63–75.
V. Wigglesworth, "Action of Inert Dusts on Insects," Nature 153 (1944) 493–494.
W. David, B. Gardiner, "Factors Influencing the Action of Dust Insecticides,"Bul Ent Res. (1950) 41 1–61.
J. Kring, "Flight Behavior of Aphids," Ann Rev Ent 17 461–493 (1972).
S. Chiu, Toxicity Studies of So–Called 'Inert' Materials with the Bean Weevil, Acanthoscelides Obtectus (Say) J Econ Ent 32 240–248 (1939).
G. Stanhill, S. Moreshet, M. Fuchs, "Effect of Increasing Foliage and Soil Reflectivity on the Yield and Water use Efficiency of Grain Sorghum," Agron J. 68 329–332 (1976).
S. Moreshet, S. Cohen, Y. Fuchs, "Effect of Increasing Foliage Reflectance on Yield, Growth and Physiological Behavior of a Dryland Cotton Crop," Crop Sci 19 863–868 (1979).
R. Yokomi, "A Preliminary Report of Reduced Infection by Spiroplamsa Citri and Virescence in Whitewash–Treated Periwinkle," Phytopathology 71 914 (1981).
D. Eveling, "Similar Effects of Suspensions of Copper Oxychloride and Kaolin on Sprayed Leaves," Ann Apply Biol. (1972) 70, 245–249.
J. Jack, J. Gilbert, "The Effect of Suspended Clay on Ciliate Population Growth Rates," Freshwater Biol (1993) 29, 385–394.
H. Uppal, S. Cheema, "Effect of Mulches and Kaolin Spray on Soil Temprature, Growth, Yield and Water Use of Barley," Ind J Agric Sci (1981) 51, 653–659.
D. Meador, "Reducing Russet on 'Golden Delicious' Apples with Silicon Dioxide Formulation Foliage Sprays," Hort Sci (1977) 12, 504–505.

(List continued on next page.)

*Primary Examiner*—S. Mark Clardy
*Assistant Examiner*—Alton Pryor
*Attorney, Agent, or Firm*—Raymond F. Keller

[57] ABSTRACT

Disclosed is a method for enhancing the photosynthesis of horticultural crops which involves treating the surface of said horticultural crop with an effective amount of one or more highly reflective particulate materials.

53 Claims, No Drawings

OTHER PUBLICATIONS

T. Babu,, S. Hussaini, B. Satyanarayana, "Effect of Pre–Storage Seed Treatments on Adult Mortality, Oviposition and Development of Callosobruchus Chinensis L.(Bruchidae:Coleoptera) and the Viability of Mungbean (Vigana Radiata (L.) Wilczek) in India," Tropical Pest Mgt (1989) 35, 397–398.

T. Babu, S. Hussaini, M. Sriramulu, M. Siddiqui, Effect of Inert Clay and Insect Growth Regulators on the development of Callosobruchus Chinesis L and the Germination of Mungbean Seed [Vigna Radiata(I) Wilczek].

R. Campbell, J. Ephgrave, "Effect of Bentonite Clay on the Growth of Gaeumannomyces Graminis var. tritici and on Its Interactions with Antagonistic Bacteria," J Gen Microbiol (1983) 129, 771–777.

J. Desmarchelier, C. Ahern, "Insecticide–Retentive Carriers 2. Fenitrothion–Impregnated Clays," Aus J Exper Agric (1988) 28, 271–8.

R. Wagner, W. Ebeling, "Lethality of Inert Dust Materials to Kalotermes Minor Hagen and Their Role as Preventivesin Structural Pest Control," J Econ Ent (1959) 52, 208–212.

J.S. Kennedy, C.O. Booth, W.J.S. Kershaw, "Host Finding by Aphids in the Field," Ann Appl. Biol (1961), 49, 1–21.

W.O. Cline, R.D. Milholland, "Root Dip Treatments for Controlling Blueberry Stem Blight Caused by Botryosphaeria Dothidea in Container–Grown Nursery Plants," Plant Disease 76, 136–138 (1992).

J. Norman, "Development of Colletotrichum Gloeosporioides f. sp. clidemiae and *Septoria passiflorae* into Two Mycroherbicides with Extended Viability," Plant Disease 79, 1029–1032 (1995).

S. K. Bhattacharyya, M. K. Basu, "Kaolin Powder as a Fungal Carrier," Appl. Envir. Microbio. 44, 751–753 (1982).

R. H. Daines, R.J. Lukens, E. Brennan, I. Leone, "Phytotoxity of Captan as Influenced by Formulation, Environment and Plant Factors," Phytopathology (1957) 47, 567–572.

FDF Yougn, JRM Thacker, DJ Curtis, "The Effects of Three Adjuvants On the Retention of Insecticide Formulations by Cabbage Leaves," J Environ. Sci. Health (1996) B31, 165–178.

G. Haukenes, BK Hjeltns, "Kinetics of the Binding of Immunoglobulins, Antibodies and Virus Haemagglutination Inhibitors to Kaolin," Biologicals (1991) 19, 31–35.

J. Han, "Use of Antitranspirant Epidermal Coatings for Plant Protection in China," Plant Dis. (1990) 74, 263–266.

O. Ziv, RA Frederiksen, "The Effect of Film–Forming Anti–Transpirants on Leaf Rust and Powdery Mildew Incidence on Wheat," Plant Path (1987) 36, 242–245.

C. Jacob, et al. "New Strategies in the Control of Major Leaf Disease of Hevea," J Myco & Plant Path (1195) 25, 120.

S. Marco, "Incidence of Nonpersistently Transmitted Viruses in Pepper Sprayed with Whitewash, Oil, and Insecticide, Alone or Combined," (1993) Plant Dis 77, 1119–1122.

Ziv, O. "Control of Septoria Leaf Blotch of Wheat and Powdery Mildew of Barley with Antitranspirant Epidermal Coating Materials," Phytopar (1983) 11, 33–38.

M. Kamp, "Control of Erysiphe Cichoracearum on Zinnia Elegans, with a Polymer–Based Antitranspirant," Hort Sci (1985) 20, 879–881.

J. Zekaria–Oren, Z Eyal, "Effect of Film–Forming Compounds on the Development of Leaf Rust on Wheat Seedlings," Plant Dis (1991) 75, 231–234.

A. Franck, M. Bar–Joseph, "Use of Netting and Whitewash Spray to Protect Papaya Plants Against Nivun Haamir (NH) Dieback Disease," Crop Prot (1992) 11, 525–528.

O. Ziv, "Effects of Bicarbonates and Film–Forming Polymers on Cucurbits Foliar Diseases," Plant Dis (1992) 76, 513–517.

TC Helvey, "Insecticidal effect of Inert Solid Diluents," Sci (1952) 116, 631–632.

HG Guy, HF Dietz "Further Investigations with Japanese Beetle Repellents," J Econ Ent (1939) 32, 248–252.

C. Conceicao, A. Mexia, A. Barbosa, "Combined Effects of Silica Aerogels and Insect Growth Regulators Against Sitophilus Zeamais Motch Infestations," Int Cong Ent pro 1996.

MRGK Nair, "Structure of Waterproofing Epicuticular Layers in Insects in Relation to Inert Dust Action," Indian J Ent (1957) 19, 37–49.

BR Bartlett, "The Action of Certain 'Inert' Dust Materials on Parasitic Hymenoptera," J Econ Ent (1951) 44, 891–896.

GL Hockenyos, "Effect of Dusts on the Oriental Roach," J Econ Ent (1933) 26, 792–794.

T. Hirano, M. Kiyota, I. Aiga, "Physical Effects of Dust on Leaf Physiology of Cucumber and Kidney Bean Plants," Envirn Poll (1995) 89, 255–261.

NKS Rao, "The Effects of Antitranspirants on Leaf Water Status, Stomatal Resistance and Yield in Tomato," J Hort Sci (1985) 60, 89–92.

DW Eveling MZ Eisa, "The Effects of a Cuticle–Damaging Kaolin On Herbicidal Phytotoxicity," Weed Res (1976) 16, 15–18.

S. Marco, O. Ziv, R. Cohen, "Suppression of Powdery Mildew in Squash by Applications of Whitewash, Clay and Antitranspirant Materials," Phytopar (1194) 22, 19–29.

SM Lipson, G. Stotzky, "Effect of Kaolinite on the Specific Infectivity of Reovirus," FEMS Micr. Let. 37, 83–88 (1986).

S. Lavie, G. Storzky, "Adhesion of the Clay Minerals Montmorillonite, Kaolinite, and Attapulgite reduces Respiration of Histoplasma Capsulatum," App & Envir Micro (1986) 51, 65–73.

MS Rajan, KR Reddy, RS Rao, GHS Reddi, "Effect of Antitranspirants and Reflectants on Pod Yield of Rainfed Groundnut," Agric Sci Dig (1981) 1, 205–206.

W. Ebeling, RJ Pence, "Termites and Other Enemies of Wood," Pest Cont Oct. 1956, 46–64.

DW Eveling, A. Bataille, "The Effect of Deposits of Small Particles on the Resistance of Leaves and Petals to Water Loss," Envirn Poll (1984) 36, 229–238.

M. Llewellyn, J. Ervaz, "Abrasive Dusts as a Mechanism for Aphid Control," Ent. Exp. & Appl. 26 (1979) 219–222.

M. Swamiappan, S Jayaraj, KC Chandy, "Effect of Activated Kaolinitic Clay on Some Storage Insects," Z. Ang. Ent. 80 (1976), 385–389.

D Permual, G. Le Patourel, "Laboratory Evaluation of Acid–Activated Kaolin to Protect Stored Paddy Against Infestation by Stored Product Insects," J Stored Prod Res 26, 149–153, 1990.

DT Lowery, MK Sears, CS Harmer, "Control of Turnip Mosaic Virus of Rutabaga With Applications of Oil, Whitewash, and Insecticides," J Econ Ent(1990) 83, 2352–2356.

S. Marco, "Incidence of Aphid–Transmitted Virus Infections Reduced by Whitewash Sprays on Plants," Amer. Phytop (1986) 76, 1344–1348.

J. Basnizki, M. Evanari, "The Influence of a Reflectant on Leaf Temperature and Development of the Globe Artichoke (*Cynara scolymus* L.)," J. Am Soc Hort Sci 100, 109–112 (1975).

EF Durner, TJ Gianfagna, "Interactions of Ethephon, Whitewashing, and Dormant Oil on Peach Pistil Growth, Hardiness and Yield," Am Hort Sci 27, 104–105 (1992).

EF Durner, TJ Gianfagna, "Peach Pistil Growth Inhibition and Subsequent Bloom Delay by Midwinter Bud Whitewashing," Am Hort Sci 25, 1222–1224 (1990).

WJ Lipton, "Temperatures and Net Heat Gain in Normal and Whitewashed Cantaloupe Fruits," J. Amer. Hort. Sci. 97, 242–244 (1972).

WJ Lipton, F. Matoba, "Whitewashing to Prevent Sunburn of 'Crenshaw' Melons," Hortscience, 6, 343–345 (1971).

WS Cranshaw, DJ Liewehr, "Effects of Colored Sprays on Aphid & Psyllid Colonization," SW Entomol 15, 205–209 (1990).

S. Marco, "Possible Modes of Action of Whitewash in Reducing Virus Incidence in Potatoes," Potato Res 33, 138–139 (1990).

I. Bar–Zakay, M. Gokkes, Y. Oren, "Chemical Control of Aphids on Citrus Bearing Trees," Phytoparasitica 15, 343 (1987).

S. Marco, "Reducing the Incidence of Aphid–Transmitted Viruses by Reflective Materials," Phytoparasitica 13, 279–280 (1985).

DJ Gumpf, GN Oldfield, RK Yokomi, "Progress in the Control of Citrus Stubborn Disease," Proc Int. Soc. Citric, 457–458 (1981).

JGM Vos, TS Uhan, B. Sutarya, "Integrated Crop Management of Hot Peppers," Crop Prot. 14, 445–452 (1995).

CG Summers, JJ Stapleton, AS Duncan, DA Hart, "Comparison of Sprayable and Film Mulches in Delaying the Onset of Aphid–Transmitted Virus Diseases in Zucchini Squash," Plant Dis (1995) 79, 1126–1131.

PC Nicot, M. Mermier, BE Vaissiere, J. Lagier, "Differential Spore Production by Botrytis Cinerea on Agar Medium and Plant Tissue Under Near–Ultraviolet Light–Absorbing Polyethylene Film," Plant Dis (1196) 80, 555–558.

JJ Stapleton, WK Asai, JE DeVay, "Use of Polymer Mulches in Integrated Pest Management Programs for Establishment of Perennial Fruit Crops," (1989) Acta Hort. 255, 161–168.

RE Byers, CG Lyons, "Effect of Chemical Deposits from Spraying Adjacent Rows on Efficacy of Peach Bloom Thinners," HortSci (1985) 20, 1076–1078.

RE Byers, KS Yoder, GE Mattus, "Reduction in Russetting of 'Golden Delicious' Apples with 2, 4, 5–TP and Other Compounds," HortScience 18:63–65 (1983).

RE Byers, DH Carbaugh, CN Presley, "'Stayman' Fruit Cracking as Affected by Surfactants, Plant Growth Regulators, and Other Chemicals," J. Amer. Soc. Hort. Sci. 115:405–411 (1990).

Stanhill et al.: "Effect of Increasing Foliage and Soil Reflectivity on the Yield and Water Use Efficiency of Grain Sorghum". Agronomy Journal, vol. 68, Mar. 1976–Apr. 1976, pp. 329–332, XP002067941.

Moreshet et al.: "Effect of Increasing Foliage Reflectance on Yield, Growth and Physiological Behavior of a Dryland Cotton Crop", Crop Science, vol. 19, Nov. 1979–Dec. 1979, p. 863–868, XP002067942.

Thompson et al.: "The Effect of Dust on Photosynthesis and its Signficance for Roadside Plants", Environmental Pollution (Series A), vol. 34, pp. 171–190, XP–002067947.

Eller et al.: Der Einfluß von Straßenstaub auf die Strahlungsabsorption durch Blatter Archiv Fur Meterorologie, Geophysik Und Bioklimatologie (Serie B), vol. 23, 1975, pp. 137–146, XP–002067948.

Ricks et al.: "Effects of Atmospheric Pollution on Deciduous Woodland—Part 3: Effects on Photosynethic pigments of Leaves on *Quercus petraea* (Mattuschka) Leibl", Environmental Pollution, vol. 8, 1975, pp. 97–106, XP–002067949.

Farmer, A. M.: "The Effects of Dust on Vegetation—A Review", Envronmental Pollution, vol. 79, 1993, pp. 63–75, XP002067943.

METHOD FOR PROVIDING ENHANCED PHOTOSYNTHESIS

CROSS-REFERENCE TO RELATED APPLICATIONS

This application is a continuation-in-part of U.S. patent application Ser. No. 08/812,301, filed Mar. 5, 1997, now U.S. Pat. No. 5,908,708 which is incorporated herein by reference for its teachings related to the invention disclosed herein.

FIELD OF THE INVENTION

The present invention is directed to a method for enhancing the photosynthesis of horticultural crops.

BACKGROUND OF THE INVENTION

Improved yield or plant productivity is a desired horticultural effect on horticultural crops that is generally limited by the amount of light, temperature, relative humidity and other uncontrollable environmental factors when pests, water and nutrients are adequately controlled. Particulate matter from a wide range of sources is generally regarded as limiting plant productivity. See for example, Farmer, "The Effects of Dust on Vegetation—A Review," *Environmental Pollution* 79:63–75 (1993).

The prior art has discussed photosynthesis and the effects of environmental stresses on plants. See, for example; Nonomora and Benson, "Methods and compositions for enhancing carbon fixation in plants," U.S. Pat. No. 5,597,400, Stanhill, G., S. Moreshet, and M. Fuchs. "Effect of Increasing Foliage and Soil Reflectivity on the Yield and Water Use Efficiency of Grain Sorghum," *Agronomy Journal* 68:329–332 (1976); Moreshet, S., Y. Cohen, and M. Fuchs. "Effect of Increasing Foliage Reflectance on Yield, Growth, and Physiological Behavior of a Dryland Cotton Crop," *Crop Science* 19:863–868 (1979), which states that "within 2 days after spraying the kaolin reduced $^{14}CO_2$ uptake (photosynthesis) by more than 20%" and "the kaolin sprays would appear to reduce transpiration more than photosynthesis"; Bar-Joseph, M. and J. Frenkel, "Spraying citrus plants with kaolin suspensions reduces colonization by the spiraea aphid (Aphis citricola van der Goot)" *Crop Protection* 2(3):371–374 (1983), which states that "The reasons for this [yield increase of Stanhill, Ibid. and Moeshet, Ibid.] are uncertain [because photosynthesis is reduced] but aphid and virus control may have contributed to this yield increase"; Rao, N. K. S., "The Effects of Antitranspirants on Leaf Water Status, Stomatal Resistance and Yield in Tomato," *J. of Horticultural Science* 60:89–92 (1985); Lipton, W. J., and F. Matoba, "Whitewashing to Prevent Sunburn of 'Crenshaw' Melons," *HortScience* 6:434–345 (1971); Proctor, J. T. A. And L. L. Creasy "Effect of Supplementary Light on Anthocyanin Synthesis in 'McIntosh' Apples," *J. Amer. Soc. Hort. Sci* 96:523–526 (1971); Lord, W. J, and D. W. Greene, "Effects of Summer Pruning on the Quality of 'McIntosh' Apples," *HortScience* 17:372–373.

Therefore, there is still a need for cost effective inert, nontoxic methods for enhancing photosynthesis of horticultural crops. The prior art teaches away from the use of highly reflective inert particles of the instant invention in that increasing reflectivity reflects photosynthetically active light, thus, reducing photosynthesis. Unexpectedly, the instant invention results in an opposite effect—enhanced photosynthesis.

SUMMARY OF THE INVENTION

This invention relates to a method for enhancing the photosynthesis of horticultural crops which comprises applying to the surface of said horticultural crop an effective amount of one or more highly reflective particulate materials, said particulate materials being finely divided, and wherein the particles as applied allow for the exchange of gases on the surface of said crop.

DETAILED DESCRIPTION OF THE INVENTION

This invention relates to a method for enhancing the photosynthesis of horticultural crops. Photosynthesis is the process by which photosynthetic plants utilize solar energy to build carbohydrates and other organic molecules from carbon dioxide and water. The conversion of carbon dioxide to such organic molecules is generally referred to as carbon fixation or photosynthesis and, in most plants, occurs by the reductive pentose phosphate cycle, generally referred to as the C-3 cycle. The study of the path of carbon in photosynthesis four decades ago (A. A. Benson (1951), "Identification of ribulose in $^{14}CO_2$ photosynthesis products" *J. Am. Chem. Soc.* 73:2971; J. R. Quayle et al. (1954), "Enzymatic carboxylation of ribulose diphosphate" *J. Am. Chem. Soc.* 76:3610) revealed the nature of the carbon dioxide fixation process in plants. The effects of enhanced photosynthesis are typically observed by increased yields/productivity, e.g., increased fruit size or production (usually measured in weight/acre), improved color, increased soluble solids, e.g. sugar, acidity, etc., and reduced plant temperature.

The horticultural crops to which this invention relate are actively growing and/or fruiting agricultural and ornamental crops and the products thereof, including those selected from the group consisting of fruits, vegetables, trees, flowers, grasses, roots, seeds and landscape and ornamental plants.

The particulate materials useful for the purposes of this invention are highly reflective. As used herein, "highly reflective" means a material having a "Block Brightness" of at least about 80 and preferably at least about 90 and more preferably at least about 95 as measured by TAPPI standard T 646. Measurements can be made on a Reflectance Meter Technidyne S-4 Brightness Tester manufactured by Technidyne Corporation which is calibrated at intervals not greater than 60 days using brightness standards (paper tabs and opal glass standards) supplied by the Institute of Paper Science, or Technidyne Corporation. Typically a particle block or plaque is prepared from 12 grams of a dry (<1% free moisture) power. The sample is loosely placed in a cylinder holder and a plunger is slowly lowered over the sample to a pressure of 29.5–30.5 psi and held for about 5 seconds. The pressure is released and the plaque is examined for defects. A total of three plaques are prepared and three brightness values are recorded on each plaque by rotating the plaque about 120 degrees between readings. The nine values are then averaged and reported.

The finely divided particulate materials useful for the purposes of this invention may be hydrophilic or hydrophobic materials and the hydrophobic materials may be hydrophobic in and of themselves, e.g., mineral talc, or may be hydrophilic materials that are rendered hydrophobic by application of an outer coating of a suitable hydrophobic wetting agent (e.g., the particulate material has a hydrophilic core and a hydrophobic outer surface).

Typical particulate hydrophilic materials useful for the purposes of this invention include: minerals, such as calcium carbonate, talc, kaolin (both hydrous and calcined kaolins, with calcined kaolins being preferred), bentonites, clays, pyrophyllite, silica, feldspar, sand, quartz, chalk, limestone, precipitated calcium carbonate, diatomaceous earth and barytes; functional fillers such as aluminum trihydrate, pyrogenic silica, and titanium dioxide.

The surfaces of such materials can be made hydrophobic by addition of hydrophobic wetting agents. Many industrial mineral applications, especially in organic systems such as plastic composites, films, organic coatings or rubbers, are dependent upon just such surface treatments to render the mineral surface hydrophobic; see, for example, Jesse Edenbaum, *Plastics Additives and Modifiers Handbook,* Van Nostrand Reinhold, New York, 1992, pages 497–500 which is incorporated herein by reference for teachings of such surface treatment materials and their application. So-called coupling agents such as fatty acids and silanes are commonly used to surface treat solid particles as fillers or additives targeted to these industries. Such hydrophobic agents are well known in the art and common examples include: organic titanates such as Tilcom® obtained from Tioxide Chemicals; organic zirconate or aluminate coupling agents obtained from Kenrich Petrochemical, Inc.; organofunctional silanes such as Silquest® products obtained from Witco or Prosil® products obtained from PCR; modified silicone fluids such as the DM-Fluids obtained from Shin Etsu; and fatty acids such as Hystrene® or Industrene® products obtained from Witco Corporation or Emersol® products obtained from Henkel Corporation (stearic acid and stearate salts are particularly effective fatty acids and salts thereof for rendering a particle surface hydrophobic).

Examples of preferred particulate materials suitable for the purposes of this invention that are commercially available from Engelhard Corporation, Iselin, N.J. are the calcined kaolins sold under the trademark Satintone® and the siloxane treated calcined kaolins sold under the trademark Translink®; and calcium carbonate commercially available from English China Clay under the trademarks Atomite® and Supermite® and stearic acid treated ground calcium carbonates commercially available from English China Clay under the trademarks Supercoat® and Kotamite®.

The term "finely divided" when utilized herein means that the particulate materials have a median individual particle size below about 10 microns and preferably below about 3 microns and more preferably the median particle size is about one micron or less. Particle size and particle size distribution as used herein are measured with a Micromeritics Sedigraph 5100 Particle Size Analyzer. Measurements were recorded in deionized water for hydrophilic particles. Dispersions were prepared by weighing 4 grams of dry sample into a plastic beaker adding dispersant and diluting to the 80 ml mark with deionized water. The slurries were then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph, e.g., 2.58 g/ml for kaolin. The sample cells are filled with the sample slurries and the X-rays are recorded and converted to particle size distribution curves by the Stokes equation. The median particle size is determined at the 50% level.

Preferably, the particulate material has a particle size distribution wherein up to 90% by weight of the particles have a particle size of under about 10 microns, preferably below about 3 microns and more preferably about one micron or less.

The particulate materials particularly suitable for use in this invention are inert and nontoxic.

As used herein "inert" particulate materials are particles that are not phytotoxic.

The particulate materials are preferably nontoxic meaning that in the limited quantities needed for effective enhanced horticultural effect such materials are not considered harmful to animals, the environment, the applicator and the ultimate consumer.

As previously discussed, this invention relates to horticultural crops wherein the surface of said crop is treated with one or more particulate materials. This treatment should not materially affect the exchange of gases on the surface of said crop. The gases which pass through the particle treatment are those which are typically exchanged through the surface skin of living plants. Such gases typically include water vapor, carbon dioxide, oxygen, nitrogen and volatile organics.

The surface of said horticultural crop is treated with an amount of one or more highly reflective particulate materials that is effective in enhancing photosynthesis of the horticultural crop. The treatment coverage of said crop is within the skill of the ordinary artesian. Less than full crop coverage is within the scope of this invention and can be highly effective, for example, neither the under surface of the crop (that which is not exposed directly to the source of light) need be treated by the method of this invention nor must the upper surface of the crop be completely covered; although full substrate coverage can provide additional benefits such as effective disease control, smoother fruit surface, reduced bark and fruit cracking, and reduced russeting. Reference is made to U.S. Ser. No. 08/972,648, filed concurrently herewith on Nov. 18, 1997, entitled "Treated Horticultural Substrates" which is incorporated herein by reference for its teachings regarding methods for achieving these additional benefits. The method of this invention may result in the residue of the treatment forming a membrane of one or more layers of highly reflective particulate materials on the crop surface.

The particulate materials useful for the purposes of this invention may be applied as a slurry of finely divided particles in a volatile liquid such as water, a low boiling organic solvent or low boiling organic solvent/water mixture. Adjuvants such as surfactants, dispersants or speaders/stickers (adhesives) may be incorporated in preparing an aqueous slurry of the particulate materials of this invention. One or more layers of this slurry can be sprayed or otherwise applied to the crop surface. The volatile liquid is preferably allowed to evaporate between coatings. The residue of this treatment may be hydrophilic or hydrophobic. Applying particles as a dust, although not being commercially practical on a large scale due to drift and inhalation hazards, is an alternative for carrying out the method of this invention.

Spreader/stickers that can be mixed with hydrophilic particles (3% or more solids in water) to aid in spraying uniform treatments on horticultural substrates are: modified phthalic glycerlol alkyd resins such as Latron B-1956 from Rohm & Haas Co.; Plant oil based materials (cocodithalymide) with emulsifiers such as Sea-wet from Salsbury lab, Inc.; Polymeric terpenes such as Pinene II from Drexel Chem. Co.; nonionic detergents (ethoxylated tall oil fatty acids) such as Toximul 859 and Ninex MT-600 series from Stephan.

The the particle treatment may be applied as one or more layers of finely divided particulate material. The amount of material applied is within the skill of one of ordinary skill in the art. The amount will be sufficent to improve photosynthesis of the crop to which these particles are applied.

Typically, this treatment will be most effective when crop surface is white in appearance. For example, this can typically be accomplished by applying from about 25 up to about 5000 micrograms of particulate material/cm$^2$ of crop surface for particles having specific density of around 2–3 g/cm$^3$, more typically from about 100 up to about 3000 and preferably from about 100 up to about 500. As the brightness of the highly reflective particles increases lesser amounts of these brighter particles are necessary to be effective for the purposes of this invention. In addition, environmental conditions such as wind and rain may reduce crop coverage of the highly reflective particulate materials and therefore it is within the scope of this invention to apply the highly reflective particles one or more times during the growing season of said horticultural crop so as to maintain the desired effect of invention.

The low boiling organic liquids useful in the present invention are preferably water-miscible and contain from 1 to 6 carbon atoms. The term "low boiling" as used herein shall mean organic liquids which have a boiling point generally no more than 100° C. These liquids enable the particulate solids to remain in finely divided form without significant agglomeration. Such low boiling organic liquids are exemplified by: alcohols such as methanol, ethanol, propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is the preferred low boiling organic liquid.

Low boiling organic liquids may be employed in applying the particles to crop substrates for the purposes of this invention. Typically, the liquids are used in an amount sufficient to form a dispersion of the particulate material. The amount of liquid is typically up to about 30 volume percent of the dispersion, preferably from about 3 up to about 5 volume percent, and most preferably from about 3.5 to about 4.5 volume percent. The particulate material is preferably added to a low boiling organic liquid to form a slurry and then this slurry is diluted with water to form an aqueous dispersion. The resulting slurry retains the particles in finely divided form wherein most of the particles are dispersed to a particle size of less than about 10 microns.

the Virginia, West Virginia and Maryland Cooperative Extension 1997 Spray Bulletin for Commercial tree Fruit Growers publication 456-419, 2) no treatment, 3) weekly application of Translink® 77 beginning in Mar. 11, 1997, 4) weekly application of calcined kaolin (Satintone® 5HP) beginning in Apr. 29, 1997, and 5) weekly application of treated calcium carbonate (SuperCoat®—commercially available from English China Clay) beginning in Apr. 29, 1997. Treatments (3) and (5) applied 25 pounds material suspended in 4 gal methanol and added to 100 gal water. Treatment (4) applied 25 pounds material suspended in 100 gal water with the addition of 27 oz Ninex® MT-603 and 2 pints Toximul. These treatments were applied at the rate of 125 gal/acre using an orchard sprayer. This mixture was applied at the rate of 125 gal/acre using an orchard sprayer. The treatments were arranged in a randomized complete block design with 4 replications and 3 trees/plot. Treatments were not irrigated and received 21.58 cm of precipitation from May 1 to Aug. 30, 1997. Fruit were harvested at maturity; fruit number, weight and color were measured. Color was measured using a Hunter calorimeter. Color values represent Hunter "a" value units, in which increasing value represents increasing red color. Photosynthesis and stomatal conductance were measured on Aug. 6 and 8, 1997. Photosynthesis and stomatal conductance data were collected using a Licor 6300 photosynthesis system. Increasing values of photosynthesis and stomatal conductance represent increasing assimilation of carbon dioxide from the atmosphere and transpiration of water from the leaf, respectively; both parameters reflect improved plant productivity when values increase. Treatments (1) and (3) were measured twice daily at 10 to 11 am and 2 to 3 pm. Three trees in each plot were measured with 2 sunlit leaves/tree. Canopy temperature was measured using an Everest Interscience (Model 110) infrared thermometer with +/−0.5° C. accuracy, in which the temperature of the plant surface approximately 1 m in diameter was determined on the sunlit side of the tree. Data for canopy temperature are presented as the difference between leaf and air temperature. A negative canopy temperature denotes a canopy cooler than air temperature due to transpiration and heat reflection. The data are reported in Table I.

TABLE I

| Treatment | Yield/tree (kg) | Fruit weight (g) | Red Color | Photosynthesis rate ($\mu$moles $CO_2/m^2$/sec) | Stomatal conductance (mol/m$^2$/sec) | Canopy Temperature (C.) |
|---|---|---|---|---|---|---|
| Conventional Control | 43.7 | 136 | 19.7 | 6.7 | 0.35 | −4.2 |
| | 30.1 | 123 | 23.2 | | | |
| Translink ® 77 | 51.6 | 135 | 23.9 | 9.2 | 0.57 | −5.2 |
| Calcined Kaolin | 37.6 | 124 | 21.0 | | | |
| Treated CaCO3 | 39.1 | 130 | 24.1 | | | −5.5 |

The following examples are illustrative of embodiments of the invention and are not intended to limit the invention as encompassed by the claims forming part of the application.

EXAMPLE 1

"Red Delicious" apple trees received the following treatments: 1) Conventional pesticide applications applied according to the presence of economic levels of pests using The use of hydrophobic kaolin (Translink® 77) increased yield compared to conventional management (51.6 vs 43.7 kg, respectively) without a meaningful reduction in fruit size (135 vs 136 g/fruit).

The use of hydrophobic kaolin (Translink® 77) improved fruit color compared to the conventional management (23.9 vs 19.7). Treated CaCO$_3$ (SuperCoat®) and calcined Kaolin (Satintone® 5HB) also improved color compared to the conventional management (24.1 and 21.0 vs 19.7). The untreated control improved color compared to the conventional management (23.2 vs 19.7) but this is likely due to defoliation of the tree due to poor pest control since no pesticides were applied (see Lord and Greene, Ibid.). Defoliation from pest damage increases light to the fruit surface which increases color development. Pest control levels were adequate in all other treatments and did not result in defoliation.

Average precipitation approximates 35.6 cm from April 1 to August 30; precipitation was 40% below normal.

The application of Translink® 77 increased photosynthesis, stomatal conductance and reduced plant temperature. Stomatal conductance is a measure of the width of stomates on the underside of the leaf. Water loss, in the form of transpiration, occurs through the stomates and is controlled by the size of the stomatal opening. The greater the size of the opening, the greater is the stomatal conductance, and so transpiration is greater. Similarly, the greater the size of the stomatal opening, the greater is the influx of carbon dioxide necessary for photosynthesis. Canopy temperature was reduced by the application of Translink® 77 due to the increased transpirational cooling of the leaf related to increased stomatal conductance resulting from the application of Translink® 77. The application of calcium carbonate (SuperCoat®) also reduced plant temperature, presumably due to increased transpirational cooling of the leaf related to increased stomatal conductance.

Yakima, Wash.

"Red Delicious" apple trees received the following treatments: 1) no treatment; this untreated control did not have pest pressures that exceeded the threshold for pesticide application, 2) application of Translink® 77 on April 5, May 8, 29; June 25; July 14; September 4, 3) application of Translink® 77 on the same dates as "(2)" and on May 22, June 9, and July 31. Treatments (2) and (3) applied 25 pounds material suspended in 4 gal methanol and added to 96 gal water. This mixture was applied at the rate of 100 gal/acre using an orchard sprayer. The treatments were arranged in a randomized complete block design with 3 replications of 3 trees/plot. Treatments were all irrigated on a weekly basis to meet plant water needs using sprinkler irrigation located beneath the trees. Photosynthesis and stomatal conductance were measured on Jul. 17 to 20, 1997. Photosynthesis data were collected using a Licor 6300 photosynthesis system. Treatments (1), (2) and (3) were measured twice daily at 10 to 11 am and 2 to 3 pm. Three trees in each plot were measured with 2 sunlight leaves/tree. Data are the mean values for all days and hours sampled. Canopy temperature was measured using an Everest Interscience Infrared (Model 110) thermometer with +/-0.5 C. accuracy, in which the temperature of the plant surface approximately 1 meter in diameter was determined on the sunlit side of the tree. Data for canopy temperature are presented as the difference between leaf and air temperature. A negative canopy temperature denotes a canopy cooler than air temperature due to transpiration and heat reflection. Canopy temperature data were collected from Aug. 17 to 20, 1997. The data presented in Table IV are representative of the entire data set. At the time of harvest, 20 fruit were randomly collected from each of the 3 trees/plot (total of 180 fruit/treatment). Fruit were weighed and color determined. Color was determined with a Hunter colorimeter. Color values represent Hunter "a" values.

TABLE II

| Treatment | Fruit weight (g/fruit) | Photosynthesis ($\mu$mol $CO_2/m^2$/sec) | Stomatal conductance (mol/$m^2$/sec) | Canopy temperature (° C.) |
|---|---|---|---|---|
| Control | 164 | 8.8 | 0.24 | −4.5 |
| Translink ® 77 applied 7 times | 177 | 11.3 | 0.43 | −5.7 |
| Translink ® 77 applied 10 times | 195 | 12.9 | 0.46 | −6.0 |

Fruit size increased with increasing applications of Translink® 77.

Trees in the study had fruit size greater than the study in Kearneysville, W. Va. due to the use of irrigation.

The reduced canopy temperature of both Translink® 77 treatments illustrates that the application of these particles can reduce plant temperature.

The application of Translink® 77 increased photosynthesis, stomatal conductance and reduced plant temperature. Canopy temperature was reduced by the application of Translink® 77 due to the increased transpirational cooling of the leaf related to increased stomatal conductance resulting from the application of Translink® 77. Reducing the frequency of application from 7 applications did reduce photosynthesis, stomatal conductance, and canopy temperature compared to 10 applications, demonstrating that there is a beneficial response to increasing amounts of Translink® 77 coverage.

EXAMPLE 3

Santiago, Chile

"September Lady" peach, spaced 4 m×6 m, received the following treatments: 1) Conventional pesticide application applied according to the presence of economic levels of pests, 2) no treatment, 3) weekly application of Translink® 77 beginning Oct. 29, 1996. Treatment (3) applied 25 pounds material suspended in 4 gal methanol and added to 96 gal water. This mixture was applied at the rate of 100 gal/acre using a high pressure hand sprayer. Treatments were irrigated weekly using surface irrigation. Fruit were harvested at maturity and the number and weight measured. The data are reported in Table III.

TABLE III

| Treatment | Yield/tree (kg) | Fruit weight (g) | Fruit number/tree |
|---|---|---|---|
| Conventional | 13.9 | 156 | 94 |
| Control | 14.6 | 139 | 109 |
| Translink ® 77 | 25.4 | 137 | 156 |

The use of hydrophobic kaolin (Translink® 77) increased yield compared to the conventional treatment and the control by increasing the number of fruit/tree. Fruit size was reduced, although not statistically, from 156 to 137 g due to the larger number of fruit on the peach tree (94 vs 156).

EXAMPLE 4

Biglerville, Pa.—Dan Pack Orchard

"Golden Delicious" apples received 3 treatments: 1) commercial pesticide application applied according to the presence of economic levels of pests using the Virginia, West Virginia and Maryland Cooperative Extension 1997 Spray Bulletin for Commercial tree Fruit Growers publication 456-419, 2) full rate of Translink® 77, and 3) half rate of Translink® 77. Treatments (2) and (3) applied 25 and 12.5 pounds material, respectively, suspended in 4 and 2 gal methanol, respectively, and added to 100 gal water. This mixture was applied at the rate of 200 gal/acre using an orchard sprayer. The treated area was approximately 1 acre plots with 2 replications of each treatment in a randomized block design. At harvest the plots were commercially harvested and processed by a commercial grading line. At the time of grading, 100 fruit from each plot were randomly chosen to determine fruit size, color, and surface defects. Color was determined using a Hunter colorimeter. Green color values represent Hunter "a" values in which higher values represent more yellow color, a beneficial trait in "Golden Delicious" apple. The data are reported in Table IV.

TABLE IV

| Treatment | Fruit size (mm) | Green color |
| --- | --- | --- |
| Translink ® 77 full rate | 69 | −8.0 |
| Translink ® 77 half rate | 67 | −8.9 |
| Conventional | 67 | −10.0 |

Application of Translink® 77 at the full and half rate reduced green color, and Translink® 77 at the full rate increased fruit size compared to the half rate and conventional treatment.

"Stayman" apples received 2 treatments: 1) commercial pesticide application applied according to the presence of economic levels of pests using the Virginia, West Virginia and Maryland Cooperative Extension 1997 Spray Bulletin for Commercial tree Fruit Growers publication 456-419, 2) Translink® 77 treatment applied 25 pounds material suspended in 4 gal methanol and added to 96 gal water. This mixture was applied at the rate of 200 gal/acre using an orchard sprayer. Each treatment was applied to 1 acre blocks with no randomization. Apples were harvested commercially and processed on a commercial grading line. Data presented represent percent packout from the commercial grading line. The data are reported in Table V.

TABLE V

| Treatment | Fruit size (mm) | <2.5 inches (%) | 2.5–2.75 inches (%) | 2.75–3.0 inches (%) | >3.0 inches (%) |
| --- | --- | --- | --- | --- | --- |
| Translink ® 77 | 69 | 11 | 38 | 44 | 7 |
| Conventional | 62 | 66 | 28 | 6 | 0 |

The application of Translink® 77 increased the packout of larger fruit and reduced the losses due to small fruit (<2.5 inches) compared to the conventional treatment.

What is claimed is:

1. A method for enhancing the photosynthesis of horticultural crops which comprises applying to the surface of said horticultural crop an effective amount of one or more highly reflective particulate materials, said particulate materials being finely divided, and wherein the particles as applied allow for the exchange of gases on the surface of said crop and the finely divided particulate materials have a median individual particle size below about 3 microns.

2. The method according to claim 1 wherein said particles have a Block Brightness of at least about 90.

3. The method of claim 1 wherein said particulate materials are hydrophobic.

4. The method of claim 1 wherein said particulate materials are hydrophilic.

5. The method of claim 1 wherein the particulate material has a particle size distribution wherein most of the particles have a particle size of under about 10 microns.

6. The method of claim 1 wherein the particulate material comprises a hydrophilic core and a hydrophobic outer surface.

7. The method of claim 6 wherein said hydrophilic core materials are selected from the group consisting of calcium carbonate, mica, kaolin, bentonite, clays, pyrophyllite, silica, feldspar, sand, quartz, chalk, limestone, diatomaceous earth, baryte, aluminum trihydrate, titanium dioxide and mixtures thereof.

8. The method of claim 4 wherein said hydrophilic materials are selected from the group consisting of calcium carbonate, talc, hydrous kaolin, calcined kaolin, bentonites, clays, pyrophyllite, silica, feldspar, sand, quartz, chalk, limestone, precipitated calcium carbonate, diatomaceous earth, barytes, aluminum trihydrate, pyrogenic silica, titanium dioxide and mixtures thereof.

9. The method of claim 6 wherein said hydrophobic outer surface materials are selected from the group consisting of organic titanates, organic zirconate or aluminate coupling agents, organofunctional silanes, modified silicone fluids and fatty acids and salts thereof.

10. The method of claim 1 wherein the horticultural crop is selected from actively growing or fruiting agricultural and ornamental crops.

11. The method of claim 1 wherein the horticultural crop is selected from the group consisting of fruits, vegetables, trees, flowers, grasses, roots, seeds and landscape and ornamental plants.

12. The method of claim 1 wherein the particulate materials have a median individual particle size below about 3 microns.

13. The method of claim 6 wherein the hydrophilic core particulate materials are selected from the group consisting of calcium carbonate, calcined kaolin and mixtures thereof.

14. The method of claim 4 wherein the hydrophilic particulate materials are selected from the group consisting of calcium carbonate, calcined kaolin and mixtures thereof.

15. A method for enhancing the photosynthesis of horticultural crops which comprises applying to the surface of an actively growing or fruiting horticultural crop selected from the group consisting of fruits, vegetables, trees, flowers, grasses, roots, seeds and landscape and ornamental plants which comprises applying to the surface of said horticultural crop an effective amount of a slurry of one or more highly reflective particulate materials having a Block Brightness of at least about 90, said materials comprising one or more particulate materials, selected from the group consisting of calcium carbonate, calcined kaolin and mixtures thereof, said particulate materials have a median individual particle size of about one micron or less, and wherein said particles as applied allow for the exchange of gases on the surface of said crop.

16. The method of claim 1 or 15 wherein the particulate materials are applied one or more times during the growing season of said horticultural crop.

17. A method for enhancing the photosynthesis of horticultural crops which comprises applying to the surface of said horticultural crop an effective amount of one or more highly reflective particulate materials, said particulate materials being finely divided, and wherein the particles as applied allow for the exchange of gases on the surface of said crop and the particles have a Block Brightness of at least about 90.

18. The method of claim 17 wherein said particulate materials are hydrophobic.

19. The method of claim 17 wherein said particulate materials are hydrophilic.

20. The method of claim 17 wherein the particulate material has a particle size distribution wherein most of the particles have a particle size of less than about 10 microns.

21. The method of claim 17 wherein the particulate material comprises a hydrophilic core and a hydrophobic outer surface.

22. The method of claim 21 wherein said hydrophilic core materials are selected from the group consisting of calcium carbonate, mica, kaolin, bentonite, clays, pyrophyllite, silica, feldspar, sand, quartz, chalk, limestone, diatomaceous earth, baryte, aluminum trihydrate, titanium dioxide and mixtures thereof.

23. The method of claim 19 wherein said hydrophilic materials are selected from the group consisting of calcium carbonate, talc, hydrous kaolin, calcined kaolin, bentonites, clays, pyrophyllite, silica, feldspar, sand, quartz, chalk, limestone, precipitated calcium carbonate, diatomaceous earth, barytes, aluminum trihydrate, pyrogenic silica, titanium dioxide and mixtures thereof.

24. The method of claim 21 wherein said hydrophobic outer surface materials are selected from the group consisting of organic titanates, organic zirconate or aluminate coupling agents, organofunctional silanes, modified silicone fluids and fatty acids and salts thereof.

25. The method of claim 17 wherein the horticultural crop is selected from the group consisting of fruits, vegetables, trees, flowers, grasses, roots, seeds and landscape and ornamental plants.

26. The method of claim 17 wherein the finely divided particulate materials have a median individual particle size below about 3 microns.

27. The method of claim 21 wherein the hydrophilic core particulate materials are selected from the group consisting of calcium carbonate, calcined kaolin and mixtures thereof.

28. The method of claim 19 wherein the hydrophilic particulate materials are selected from the group consisting of calcium carbonate, calcined kaolin and mixtures thereof.

29. A method for enhancing the photosynthesis of horticultural crops which comprises applying to the surface of said horticultural crop an effective amount of one or more highly reflective particulate materials, said particulate materials being finely divided, and wherein the particles as applied allow for the exchange of gases on the surface of said crop and the particulate materials are hydrophobic wherein said particles have a Block Brightness of at least about 80.

30. The method according to claim 29 wherein said particles have a Block Brightness of at least about 90.

31. The method of claim 29 wherein the particulate material has a particle size distribution wherein most of the particles have a particle size of under about 10 microns.

32. The method of claim 29 wherein the particulate material comprises a hydrophilic core and a hydrophobic outer surface.

33. The method of claim 32 wherein said hydrophilic core materials are selected from the group consisting of calcium carbonate, mica, kaolin, bentonite, clays, pyrophyllite, silica, feldspar, sand, quartz, chalk, limestone, diatomaceous earth, baryte, aluminum trihydrate, titanium dioxide and mixtures thereof.

34. The method of claim 32 wherein said hydrophobic outer surface materials are selected from the group consisting of organic titanates, organic zirconate or aluminate coupling agents, organofunctional silanes, modified silicone fluids and fatty acids and salts thereof.

35. The method of claim 29 wherein the horticultural crop is selected from the group consisting of fruits, vegetables, trees, flowers, grasses, roots, seeds and landscape and ornamental plants.

36. The method of claim 29 wherein the finely divided particulate materials have a median individual particle size below about 3 microns.

37. The method of claim 32 wherein the hydrophilic core particulate materials are selected from the group consisting of calcium carbonate, calcined kaolin and mixtures thereof.

38. A method for enhancing the photosynthesis of horticultural crops which comprises applying to the surface of said horticultural crop an effective amount of one or more highly reflective particulate materials, said particulate materials being finely divided, and wherein the particles as applied allow for the exchange of gases on the surface of said crop and the particulate materials have a particle size distribution wherein most of the particles have a particle size of under about 10 microns.

39. The method of claim 38 wherein said particulate materials are hydrophobic.

40. The method of claim 38 wherein said particulate materials are hydrophilic.

41. The method of claim 38 wherein the particulate material comprises a hydrophilic core and a hydrophobic outer surface.

42. The method of claim 41 wherein said hydrophilic core materials are selected from the group consisting of calcium carbonate, mica, kaolin, bentonite, clays, pyrophyllite, silica, feldspar, sand, quartz, chalk, limestone, diatomaceous earth, baryte, aluminum trihydrate, titanium dioxide and mixtures thereof.

43. The method of claim 40 wherein said hydrophilic materials are selected from the group consisting of calcium carbonate, talc, hydrous kaolin, calcined kaolin, bentonites, clays, pyrophyllite, silica, feldspar, sand, quartz, chalk, limestone, precipitated calcium carbonate, diatomaceous earth, barytes, aluminum trihydrate, pyrogenic silica, titanium dioxide and mixtures thereof.

44. The method of claim 41 wherein said hydrophobic outer surface materials are selected from the group consisting of organic titanates, organic zirconate or aluminate coupling agents, organofunctional silanes, modified silicone fluids and fatty acids and salts thereof.

45. The method of claim 38 wherein the horticultural crop is selected from the group consisting of fruits, vegetables, trees, flowers, grasses, roots, seeds and landscape and ornamental plants.

46. The method of claim 41 wherein the hydrophilic core particulate materials are selected from the group consisting of calcium carbonate, calcined kaolin and mixtures thereof.

47. The method of claim 40 wherein the hydrophilic particulate materials are selected from the group consisting of calcium carbonate, calcined kaolin and mixtures thereof.

48. A method for enhancing the photosynthesis of horticultural crops which comprises applying to the surface of said horticultural crop an effective amount of one or more highly reflective particulate materials, said particulate materials being finely divided, and wherein the particles as applied allow for the exchange of gases on the surface of said crop and the particulate materials comprise a hydrophilic core and a hydrophobic outer surface.

49. The method of claim 48 wherein said hydrophilic core materials are selected from the group consisting of calcium carbonate, mica, kaolin, bentonite, clays, pyrophyllite, silica, feldspar, sand, quartz, chalk, limestone, diatomaceous earth, baryte, aluminum trihydrate, titanium dioxide and mixtures thereof.

50. The method of claim 48 wherein said hydrophobic outer surface materials are selected from the group consisting of organic titanates, organic zirconate or aluminate coupling agents, organofunctional silanes, modified silicone fluids and fatty acids and salts thereof.

51. The method of claim 48 wherein the horticultural crop is selected from actively growing or fruiting agricultural and ornamental crops.

52. The method of claim 48 wherein the finely divided particulate materials have a median individual particle size below about 3 microns.

53. The method of claim 48 wherein the hydrophilic core particulate materials are selected from the group consisting of calcium carbonate, calcined kaolin and mixtures thereof.

* * * * *

UNITED STATES PATENT AND TRADEMARK OFFICE
CERTIFICATE OF CORRECTION

PATENT NO. : 6,110,867
DATED : August 29, 2000
INVENTOR(S) : David Michael Glenn, Dennis G. Sekutowski, Gary J. Puterka It is certified that error appears in the above-indentified patent and that said Letters Patent is hereby corrected as shown below:

On the title page, item: [73], the Assignees should read "Engelhard Corporation, Iselin, New Jersey USA" and "The United States of America, as represented by the Secretary of Agriculture, Washington, D.C., USA".

Signed and Sealed this

Eighth Day of May, 2001

Attest:

NICHOLAS P. GODICI

Attesting Officer   Acting Director of the United States Patent and Trademark Office

US006110867C1

(12) EX PARTE REEXAMINATION CERTIFICATE (5292nd)
United States Patent
Glenn et al.

(10) Number: US 6,110,867 C1
(45) Certificate Issued: *Mar. 7, 2006

(54) METHOD FOR PROVIDING ENHANCED PHOTOSYNTHESIS

(75) Inventors: David Michael Glenn, Shepherdstown, WV (US); Dennis G. Sekutowski, Stockton, NJ (US); Gary J. Puterka, Sheperdstown, WV (US)

(73) Assignees: Engelhard Corporation, Iselin, NJ (US); The United States of America as represented by the Secretary of Agriculture, Washington, DC (US)

Reexamination Request:
No. 90/006,658, Jun. 6, 2003

Reexamination Certificate for:
Patent No.: 6,110,867
Issued: Aug. 29, 2000
Appl. No.: 08/972,659
Filed: Nov. 18, 1997

( * ) Notice: This patent is subject to a terminal disclaimer.

Certificate of Correction issued May 8, 2001.

Related U.S. Application Data

(63) Continuation-in-part of application No. 08/812,301, filed on Mar. 5, 1997, now Pat. No. 5,908,708.

(51) Int. Cl.
*A01N 59/00* (2006.01)
*A01N 59/06* (2006.01)
*A01N 55/02* (2006.01)
*A01N 57/00* (2006.01)

(52) U.S. Cl. ............... 504/119; 504/120; 504/126; 504/127; 504/187; 504/188; 504/367

(58) Field of Classification Search .......... 504/119, 504/120, 126, 127, 187, 188, 367
See application file for complete search history.

(56) References Cited

U.S. PATENT DOCUMENTS 6,069,112 A * 5/2000 Glenn et al. .............. 504/119

OTHER PUBLICATIONS

Eveling, Effects of Spraying Plants with Suspensions of Inert Dusts, Ann. Appl. Biol., 1969, p. 139.
Moreshet, Effect of Increasing Foliage Reflection of Yield, Growth . . . , Crop Science, 1979, p. 863.
Vijayakumar, Prevention of Photo–Induced Chlorophyll Loss . . . , Ag. and Forest Met., 1985, p. 17.
TAPPI Press, Physical Chemistry of Pigments in Paper Coatings, 1977, pp. ix, 11–14.
TAPPI Press, Pigments for Paper, 1984, pp. xii–xiii, 53, 95, 132–135, 241.
Hecht, Optics, 2nd Ed., 1987, p. 294.
Tegethof, Calcium Carbonate—From the Cretaceous Period into the 21st Century, 2001, pp. 225–229.
Engelhard, Kaolins for the Paper Industry, Dec. 1985.
Federation of Societies for Coatings Technology (FCST), Data Sheets, 1981, pp. 10–13, 24–27.
Kittel (German–language data sheet), Textbook for Lacquers and Coatings, 1974, p. 372.
Columbia River Carbonate, Microna S–90, Dec. 1995.
Columbia River Carbonate, Microna S–93, Dec. 1995.

* cited by examiner

*Primary Examiner*—John Pak

(57) ABSTRACT

Disclosed is a method for enhancing the photosynthesis of horticultural crops which involves treating the surface of said horticultural crop with an effective amount of one or more highly reflective particulate materials.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 12 is cancelled.

Claims 1, 15, 17, 29, 38 and 48 are determined to be patentable as amended.

Claims 2–11, 13–14, 16, 18–28, 30–37, 39–47 and 49–53, dependent on an amended claim, are determined to be patentable.

1. A method for enhancing [the] photosynthesis of *a* horticultural crop[s] *by increasing carbon dioxide assimilation of said horticultural crop* which comprises applying to the surface of said horticultural crop an effective amount of one or more highly reflective particulate materials, said particulate materials being finely divided, and wherein the particles as applied allow for the exchange of gases on the surface of said crop and the finely divided particulate materials have a median individual particle size below about 3 microns.

15. A method for enhancing [the] photosynthesis of *a* horticultural crop[s] *by increasing carbon dioxide assimilation of said horticultural crop* which comprises applying to the surface of an actively growing or fruiting horticultural crop selected from the group consisting of fruits, vegetables, trees, flowers, grasses, roots, seeds and landscape and ornamental plants [which comprises applying to the surface of said horticultural crop] an effective amount of a slurry of one or more highly reflective particulate materials having a Block Brightness of at least about 90, said materials comprising one or more particulate materials, selected from the group consisting of calcium carbonate, calcined kaolin and mixtures thereof, said particulate materials have a median individual particle size of about one micron or less, and wherein said particles as applied allow for the exchange of gases on the surface of said crop.

17. A method for enhancing [the] photosynthesis of *a* horticultural crop[s] *by increasing carbon dioxide assimilation of said horticultural crop* which comprises applying to the surface of said horticultural crop an effective amount of one or more highly reflective particulate materials, said particulate materials being finely divided, and wherein the particles as applied allow for the exchange of gases on the surface of said crop and the particles have a Block Brightness of at least about 90.

29. A method for enhancing [the] photosynthesis of *a* horticultural crop[s] *by increasing carbon dioxide assimilation of said horticultural crop* which comprises applying to the surface of said horticultural crop an effective amount of one or more highly reflective particulate materials, said particulate materials being finely divided, and wherein the particles as applied allow for the exchange of gases on the surface of said crop and the particulate materials are hydrophobic wherein said particles have a Block Brightness of at least about 80.

38. A method for enhancing [the] photosynthesis of *a* horticultural crop[s] *by increasing carbon dioxide assimilation of said horticultural crop* which comprises applying to the surface of said horticultural crop an effective amount of one or more highly reflective particulate materials, said particulate materials being finely divided, and wherein the particles as applied allow for the exchange of gases on the surface of said crop and the particulate materials have a particle size distribution wherein most of the particles have a particle size of under about 10 microns.

48. A method for enhancing [the] photosynthesis of *a* horticultural crop[s] *by increasing carbon dioxide assimilation of said horticultural crop* which comprises applying to the surface of said horticultural crop an effective amount of one or more highly reflective particulate materials, said particulate materials being finely divided, and wherein the particles as applied allow for the exchange of gases on the surface of said crop and the particulate materials comprise a hydrophilic core and a hydrophobic outer surface.

\* \* \* \* \*